United States Patent [19]
Griffith, III et al.

[11] Patent Number: 5,470,318
[45] Date of Patent: Nov. 28, 1995

[54] CATHETER/NEEDLE ASSEMBLY KIT AND METHOD FOR ADMINISTERING THERAPEUTIC AGENTS TO THE SUBARACHNOID SPACE

[75] Inventors: Richard L. Griffith, III, Schenectady, N.Y.; Joseph J. Gregg, Hasbrouck Heights; George Yurkewych, Parsippany, both of N.J.

[73] Assignee: Becton, Dickinson and Company, Franklin Lakes, N.J.

[21] Appl. No.: 326,569

[22] Filed: Oct. 20, 1994

Related U.S. Application Data

[63] Continuation of Ser. No. 11,056, Jan. 29, 1993, abandoned.
[51] Int. Cl.$^6$ .................................................. A61M 5/178
[52] U.S. Cl. ........................ 604/161; 604/93; 604/158
[58] Field of Search .................... 604/158, 162, 604/164, 239, 272, 167, 161; 206/370, 828

[56] References Cited

U.S. PATENT DOCUMENTS

| | | | |
|---|---|---|---|
| 4,723,550 | 2/1988 | Bales et al. | 128/344 |
| 4,857,057 | 8/1989 | Sanagi | 604/164 |
| 4,925,448 | 5/1990 | Bazaral | 604/171 |
| 5,085,631 | 2/1992 | Leighton | 604/28 |
| 5,178,282 | 1/1993 | Williams | 206/570 |

FOREIGN PATENT DOCUMENTS

| | | | |
|---|---|---|---|
| 9108785 | 6/1991 | WIPO | 604/158 |

*Primary Examiner*—Corrine M. Maglione
*Assistant Examiner*—Bryan L. Tsosie
*Attorney, Agent, or Firm*—Arthur D. Dawson

[57] ABSTRACT

The invention is a catheter/needle assembly for delivery of a medicament to the subarachnoid space of a patient which includes an elongate flexible tube portion sized to fit within the bore of an epidural needle. The flexible tube portion includes a proximal end, a distal end, and a hollow bore therethrough. The assembly further includes an elongate needle portion having a distal point and a passageway therethrough. The needle portion is fit within, fixedly attached to and fluidly sealed to the bore of the tube. The needle point projects distally a distance beyond the distal end of the tube so that the distal end of the tube forms a shoulder projecting radially outwardly at the needle portion.

The invention also includes a method of using the instantly invented assembly to deliver a medicament into the subarachnoid space of a patient.

The invention further includes a kit for practicing the instantly invented method of introducing a medicament into the subarachnoid space of a patient using the instantly invented assembly described hereinabove. The kit includes an epidural needle and the assembly described hereinabove. The kit may further include stylets, adapters and other accessories to allow introduction of the epidural needle, the instantly invented assembly and to facilitate attachment of a delivery device to the assembly for delivery of a medicament into the subarachnoid space of a patient.

21 Claims, 4 Drawing Sheets

CATHETER/NEEDLE ASSEMBLY KIT AND METHOD FOR ADMINISTERING THERAPEUTIC AGENTS TO THE SUBARACHNOID SPACE

This application is a continuation of U.S. application Ser. No. 08/011,056, filed Jan. 29, 1993, now abandoned.

BACKGROUND OF THE INVENTION

1. Field of Invention

The present invention relates to catheter/needle placement and more particularly to a catheter assembly including a needle and a method for its use in delivering medicaments into the subarachnoid space.

2. Description of Related Information

Generally speaking, there are two basic techniques for introducing injectable medicament into the spinal area of a patient. The techniques both can be used to create spinal anesthesia: one being delivery of the medicament into the epidural space, "epidural," and the other, delivery into the subarachnoid space, "spinal" or "subarachnoid." The medicaments can be any type of liquid therapeutic material including antibiotics, steroids and the like, but generally are agents used for anesthesia and analgesia.

A survey of previous patent literature reports in this general area is found in U.S. Pat. No. 5,085,631 which teaches a method for placement of a subarachnoid catheter which utilizes a three component apparatus comprising an outer needle, an inner needle and a catheter intermediate the two needles.

A subarachnoid placement is recognized as providing a faster, more uniform distribution of an anesthetic agent, but several major side effects may result from improper subarachnoid placement.

Puncture of the dural membrane for entrance of a needle or catheter with a large gauge needle may result in postoperative leakage of cerebrospinal fluid from the puncture site, often resulting in severe headaches. When puncture of the dural membrane is made with a needle, a bolus introduction of the anesthetic agent generally is administered. The bolus results in rapid onset of anesthesia, but the anesthetic effect then generally lasts only a few hours. To overcome both the effects of a procedure requiring a large puncture of the dural membrane and the somewhat limited duration of subarachnoid bolus delivery, microcatheters were developed. The use of these microcatheters allowed intermittent installation of the medicament for maintenance of the anesthetic effect and minimized the size of the dural puncture, thereby reducing the incidence of post procedure headaches. Microcatheters also present severe side effects. Since they are small and flexible, microcatheters have limited flow capacity, the limited flow capacity may hinder mixing the medicament with cerebrospinal fluid. Microcatheters are additionally prone to kinking. Further, there have been occurrences of permanent nerve damage with microcatheters, apparently as a result of high local concentrations of the medicament developing during delivery at adjacent branching nerves. This potential for nerve damage resulted in restrictions on the use of certain microcatheter procedures.

Subarachnoid placement of medicaments, if done properly, is acknowledged to be desirable. Thus, a method and device that would minimize the size of the puncture of the dural membrane, allow accurate and controlled placement of a therapeutically effective amount of a medicament within the subarachnoid space, thereby avoiding nerve damage, coupled with an ability to rapidly initiate and maintain a therapeutic level for longer procedures would represent an advance to the medical arts. A method and apparatus that addresses these needs constitute the present invention.

SUMMARY

A catheter/needle assembly of the present invention for introducing an injectable medicament into the subarachnoid space of a patient includes an elongate flexible tube portion sized to fit within the bore of an epidural needle. The tube has a proximal end, a distal end and a hollow bore. The assembly also includes an elongate needle portion that has a passageway through it, and a distal point. The needle portion is fit within, fixedly attached to and fluidity sealed to the bore of the flexible tube so that the passageway of the needle portion is fluidity communicative with the bore of the tube portion. The needle portion projects distally from the tube with the distal end of tube forming a shoulder projecting radially outwardly from the needle portion.

A method for using the instantly invented assembly includes providing an epidural needle with a proximal hub, a distal point and a bore therethrough. The method further includes providing a catheter/needle assembly. The assembly includes an elongate flexible tube portion sized to fit within the bore of the epidural needle. The assembly has a proximal end, a distal end and a hollow bore therethrough. The assembly further includes a needle portion being fit within, fixedly attached and fluidity sealing the bore of the flexible tube. The needle portion has a distal point and a passageway therethrough that is fluidity communicative with the bore of the flexible tube. The needle portion projects distally a distance from the distal end of the tube, the distal end of the tube forming a shoulder projecting radially outwardly from the needle portion.

The method includes introducing the epidural needle into the epidural space of the patient until the distal point of the epidural needle is in close approximation to the dural membrane. The next step of the method includes advancing the catheter/needle assembly through the bore of the epidural needle until the needle portion penetrates the dural membrane and the bore of the assembly is in fluid communication with the subarachnoid space. In practicing the method, the shoulder at the distal end of the tube substantially prevents further penetration of assembly into the dural membrane. The method then includes introducing the medicament into the subarachnoid space of the patient through the bore of the assembly.

The instant invention also includes a kit for practicing the method of introducing an injectable medicament into the subarachnoid space of patient. The kit includes an epidural needle having a distal tip and a hollow bore therethrough. The kit further includes a spinal catheter/needle assembly including an elongate flexible tube portion sized to fit within the bore of the epidural needle. The tube has a proximal end, a distal end and a passageway therethrough. The assembly further includes an elongate needle portion having a point and a passageway therethrough. The needle portion is fit within, fixedly attached to and fluidity sealed to the bore of the tube so that the point projects a distance distally and the bore of the needle portion is in fluid communication with the bore of the tube. The distal end of the tube forms a shoulder projecting radially outwardly at the needle portion.

The kit may further include a stylet for occluding the tip of the epidural needle, a guide wire stylet for the assembly, a filter and an adapter for attachment of a delivery device to the proximal end of the flexible tube. Further, the kit may be sealed in a unit package that serves as a barrier for microorganisms then subjected to conditions that render nonviable any microorganisms contained in the package.

DETAILED DESCRIPTION

Figure 1:
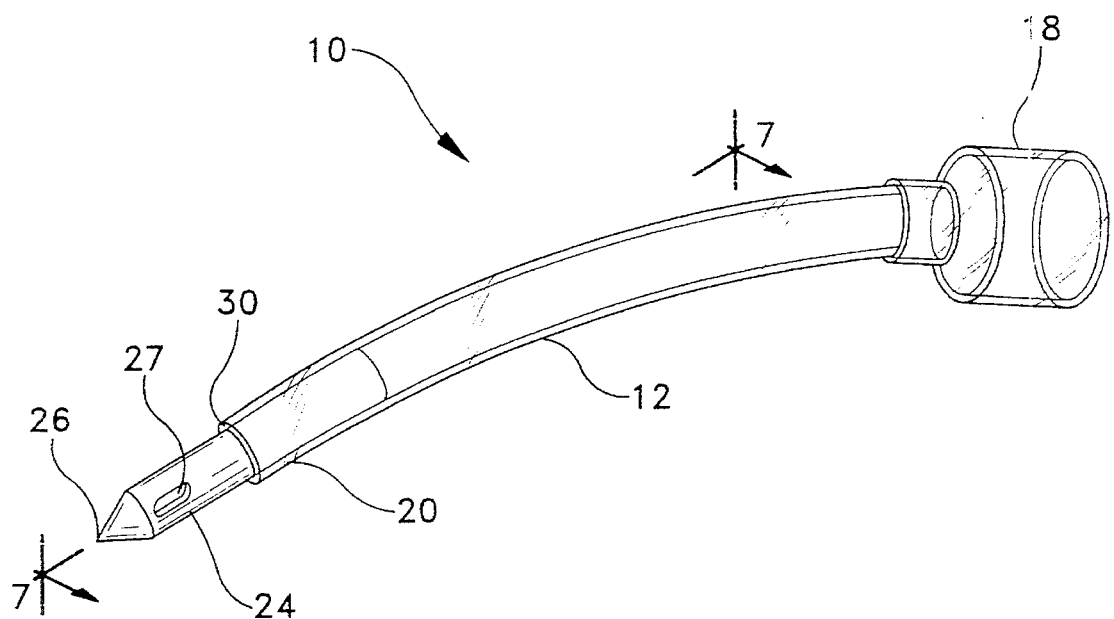
FIG. 1 is a perspective view of the catheter/needle assembly of the present invention.

While this invention is satisfied by embodiments in many different forms, there is shown in the drawings and will herein be described in detail preferred embodiments of the invention with the understanding that the present disclosure is to be considered exemplary of the principles of the invention and is not intended to limit the invention to the embodiments illustrated. The scope of the invention will be measured by the appended claims and their equivalents.

For the purposes of the description of the present invention, the term "distal end" is meant to refer to the end of the assembly closest to the needle portion point, whereas the term "proximal end" is meant to refer to the end of the assembly furthest from the needle portion point.

Adverting to FIGS. 1–8, a catheter/needle assembly 10 of the present invention is used for introducing an injectable medicament into the subarachnoid space of a patient. The injectable medicament can be any type of liquid therapeutic agent, including antibiotics, steroids and the like, but generally are agents used for anesthesia and analgesia. The assembly 10 includes an elongate flexible tube portion 12 sized to fit within a bore 14 of an epidural needle 16. Tube 12 has a proximal end 18, a distal end 20 and a hollow bore 22. Assembly 10 also includes an elongate needle portion 24 having a distal point 26 and a passageway 28 therethrough in fluid communication with bore 22 of tube 12. Needle portion 24 is fit within bore 22, being fixedly attached to and fluidity sealing bore 22. Distal end 20 of flexible tube 12 forms a shoulder 30 that projects radially outwardly from needle portion 24.

Needle portion 24 is preferably formed from stainless steel, most preferably from stainless steel having the composition 304. Needle portion 24 has an overall length "A" that is preferably about 15 to 25 mm. long and most preferably about 19 mm. Needle portion 24 projects from tube 12 a distance "B" that preferably is about 9 to 13 mm and most preferably is about 11 mm. Needle portion 24 is preferably 25 to 30 gauge and most preferably 27 gauge. Needle portion 24 preferably has a pencil point configuration and at least one side opening 27. The side opening or openings combined with bore 22, which most preferably accommodates the 27 gauge needle and thus is larger than most bores of previously used microcatheters, are believed to facilitate mixing of the medicament with cerebrospinal fluid during the delivery and thereby substantially reduce nerve damage caused by high local medicament concentration.

One skilled in the art of needles will recognize that the sizing of hypodermic needles is commonly referred to a gauge table wherein the nominal sizing of the inner and outer diameters generally corresponds to:

| Table of Hypodermic Tubing Nominal Sizes | | |
|---|---|---|
| Gauge | Outside Diameter (mm) | Inside Diameter (mm) |
| 30 | 0.30 | 0.18 |
| 29 | 0.33 | 0.20 |
| 28 | 0.36 | 0.20 |
| 27 | 0.40 | 0.25 |
| 26 | 0.46 | 0.30 |
| 25 | 0.51 | 0.30 |
| 24 | 0.56 | 0.36 |
| 23 | 0.64 | 0.38 |
| 22 | 0.71 | 0.46 |
| 21 | 0.82 | 0.56 |
| 20 | 0.90 | 0.65 |
| 19 | 1.08 | 0.80 |
| 18 | 1.27 | 0.96 |
| 17 | 1.50 | 1.17 |
| 16 | 1.65 | 1.32 |

Epidural needle 16 with bore 14, which tube 12 is sized to fit within, is sized from 16 to 25 gauge, with tube 12 being sized appropriately, for example, an epidural needle size 20 gauge with a tube portion size 0.6 mm and needle portion size 27 gauge. The overall length of assembly 10 from tube portion proximal end 18 to needle portion distal point 26 is preferably within 50 to 100 cm and most preferably has, for an adult patient, an overall length of about 76 cm. All dimensions of the most preferred embodiment present herein are intended for an average 70 kg adult. One skilled in the art of catheters, needles and hypodermic delivery devices will recognize that for specialty applications such as neonates, pediatric patients and other specialty applications, it may be desirable to reduce or increase sizes and length of some or all the components for the specific application.

Figure 2:
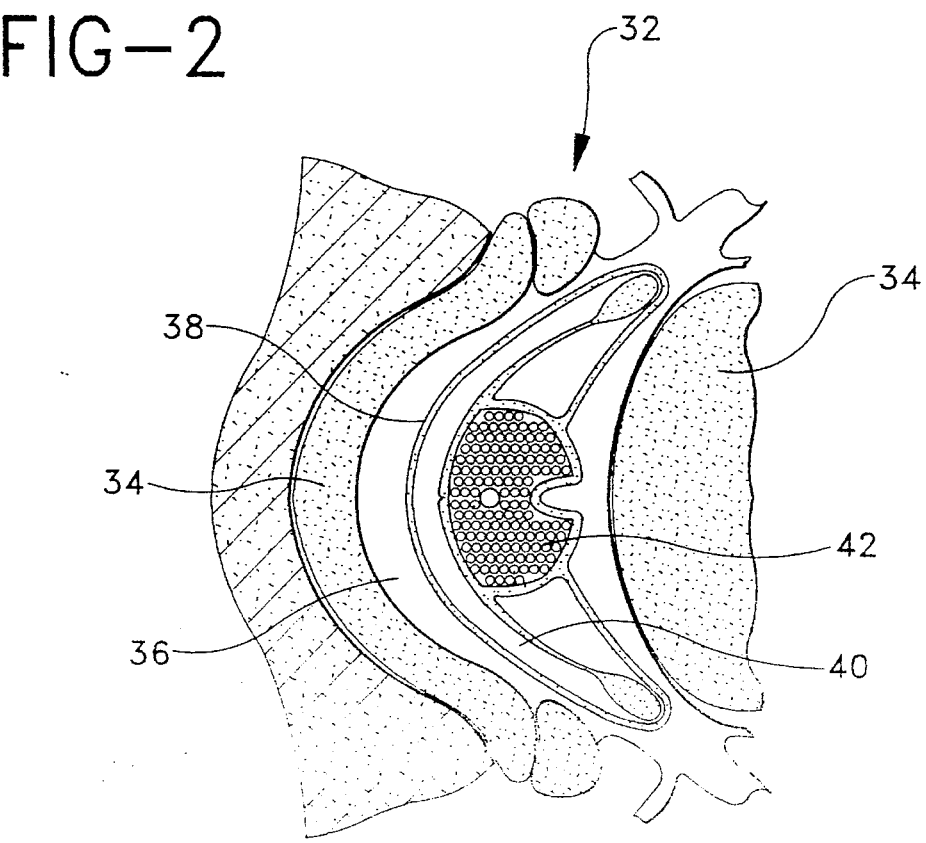
FIG. 2 is a horizontal cross-sectional view of a human spine.
Figure 3:
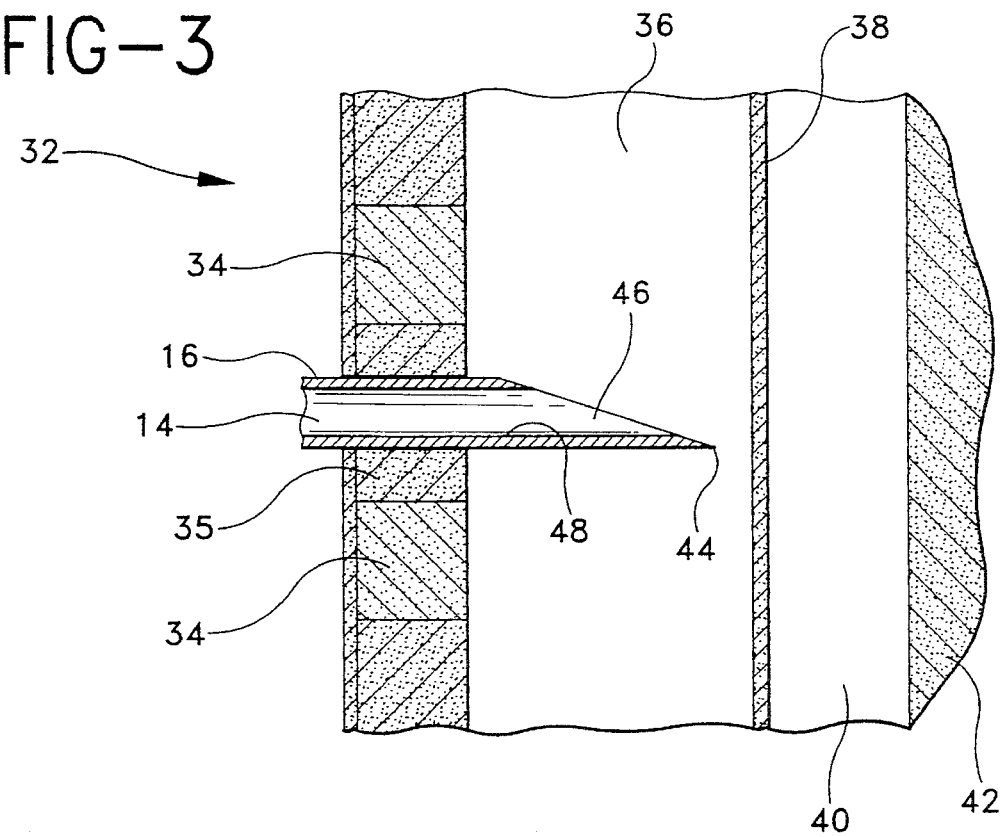
FIG. 3 is a schematic vertical cross-section of a human spine showing the placement of an epidural needle.
Figure 4:
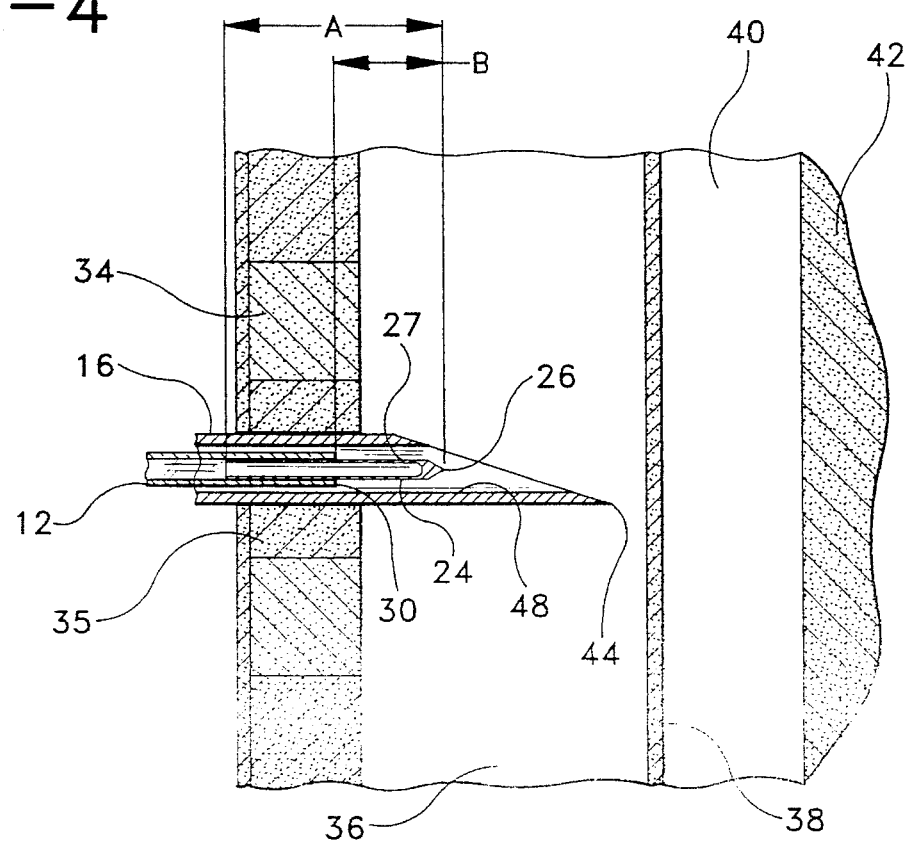
FIG. 4 is a schematic vertical cross-section of a human spine showing the introduction of the presently invented catheter/needle assembly into the bore of the epidural needle.
Figure 5:
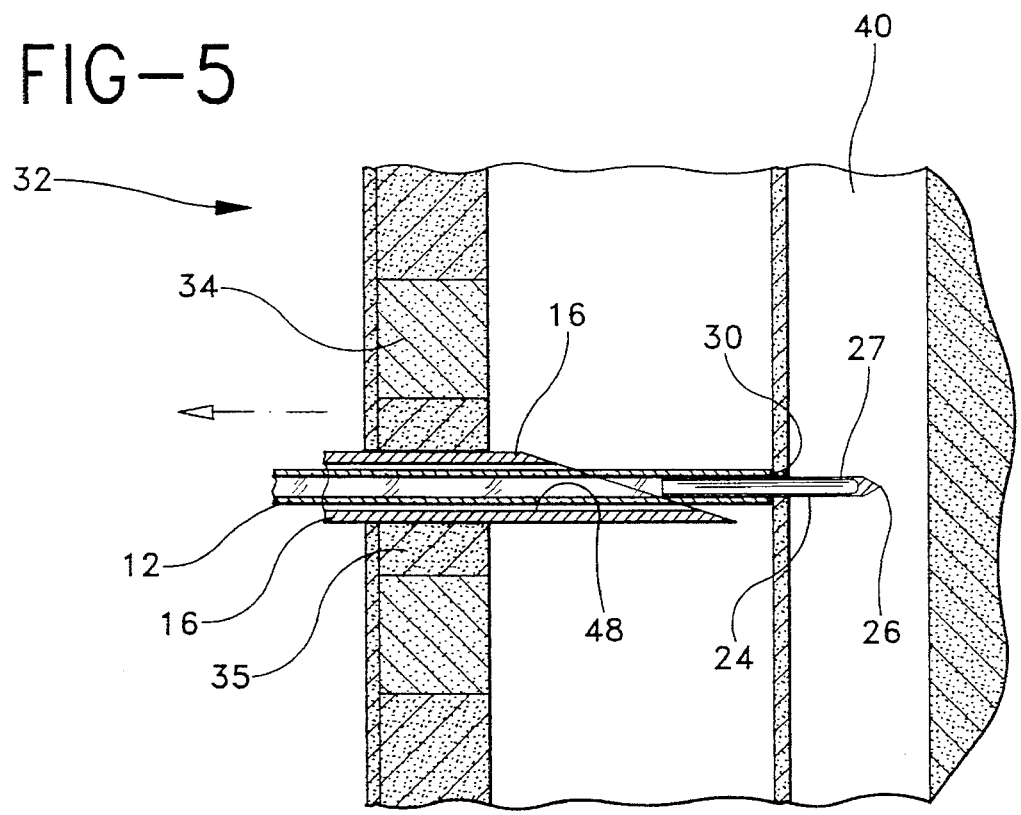
FIG. 5 is a schematic vertical cross-section of a human spine showing the advancement of the presently invented assembly through the bore of the epidural needle so that the needle portion penetrates the dural membrane.
Figure 6:
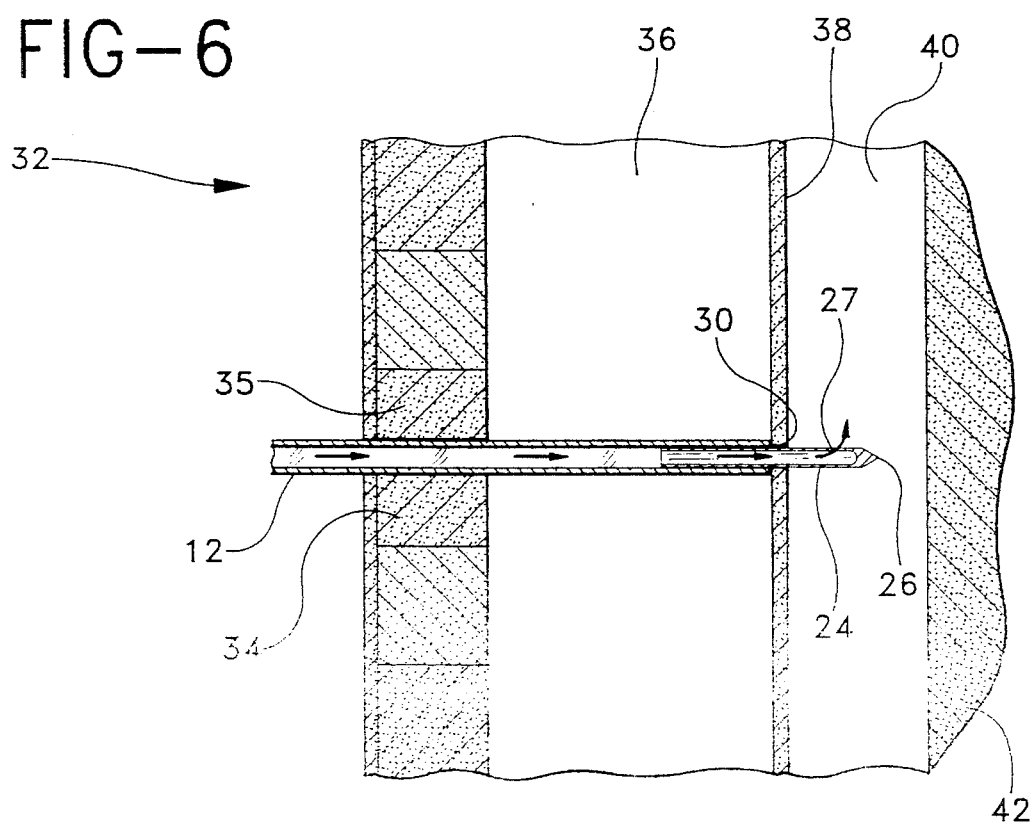
FIG. 6 is a schematic vertical cross-section of a human spine showing the presently invented assembly in position for delivery of a medicament into the subarachnoid space, the epidural needle having been removed.

A preferred method for use of assembly 10 can best be understood by reference to FIGS. 2–6. FIG. 2 shows a horizontal cross-section of a human spine 32, bone tissue 34, epidural space 36, dural membrane 38, subarachnoid space 40 and cauda equina 42. Adverting to FIGS. 3–6, a schematic vertical cross-section of spine 32 is shown with bone tissue sections 34 having ligamentous tissue 35 therebetween. Epidural needle 16 having a proximal hub, a bore 14 and a point 44 is introduced into epidural space 36 through ligamentous tissue 35 until point 44 is in close approximation to dural membrane 38. An opening 46 at distal point 44 to bore 14 of the epidural needle maybe occluded during insertion through the external skin and ligamentous tissue 35 by a suitable stylet, (not shown) to avoid transporting fragments of tissue into epidural space 36. The stylet may then be removed and replaced with assembly 10.

Assembly 10 is then advanced within bore 14 of epidural needle 16 until needle portion 24 penetrates dural membrane 38 and tube bore 22 is in fluid communication with the subarachnoid space 40. The preferred embodiment of assembly 10 is generally placed in the lumbar region of the spine. In the lumbar region, subarachnoid space 40 contains the cauda equina 42, literally translated as "horse's tail". The reason for this name is that the spinal cord usually ends at the lower border of the first lumbar vertebra, becoming a series of discrete nerves contained within the dural sac. A preferred pencil point distal tip 26 of needle portion 24 will tend to separate rather than cut these discrete nerves.

Shoulder 30 at distal end 20 of tube 12 may indicate correct depth of penetration by substantially preventing further penetration of assembly 10 into dural membrane 38. Correct placement of needle portion 24 in subarachnoid space 40 may be further confirmed by withdrawal of cerebrospinal fluid through the assembly. Following the placement of assembly 10, epidural needle 16 may be removed leaving only assembly 10. An adapter, preferably a Tuohy-Borst type adapter and the like, and a medicament filter may be fitted to proximal end 18 of tube portion 12. A delivery device many then be attached and the desired medicament administered to the patient either as a bolus, intermittent dosing, continuous infusion or a combination of these administration techniques as appropriate for the procedure to be practiced.

Figure 7:
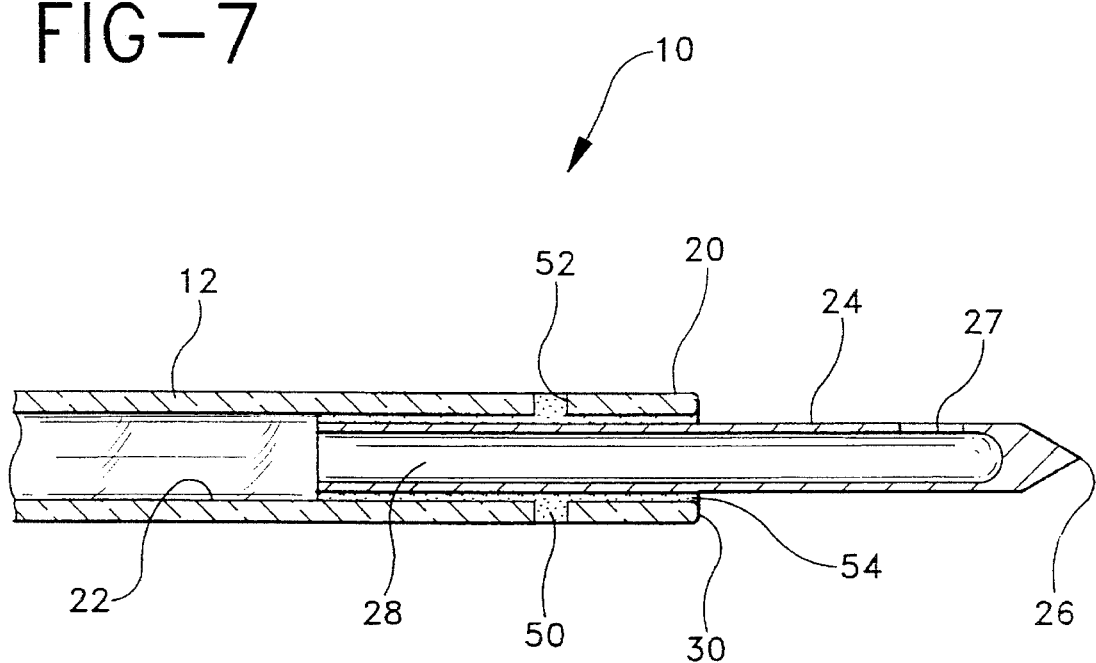
FIG. 7 is an enlarged cross-section of an embodiment of the distal portion of the assembly of the present invention.

A kit suitable for practicing the method described herein above may include epidural needle 16 and assembly 10. Needle 16 is preferably an epidural needle with a straight bevel point formed at an angle of about 30 to 50 degrees to a longitudinal axis of the needle. More preferably, needle 16 is a Crawford type needle having a straight bevel point formed at an angle of about 40 degrees to the longitudinal axis of the needle and having a size about 20 gauge with a length of about 90 mm. Epidural needle 16 may include a removable stylet to occlude opening 46 at distal point 44. The function of a stylet in an epidural needle is to prevent coring of soft tissue by the large bore needle, which could result in transport of tissue particulates into the epidural space. Flexible tube portion 12 would then preferably be sized about 0.62 mm to fit within the 0.65 mm bore of the 20 g needle 16. Needle portion 24 would preferably be 27 gauge and fixedly attached within bore 22 of tube 12. Needle portion 24 preferably has pencil point type distal tip 26 and at least one side port opening to passageway 28. As is shown in FIG. 7, needle portion 24 may be adhesively bonded to tube bore 22 by adhesives such as cyanoacrylates, epoxies, hot-melts and the like. These adhesives must serve to form a bond between the tube material and the stainless steel needle portion, as well as sealing the tube bore to the needle bore.

Flexible tube 12 may be formed from a variety of flexible materials including polyamide, polyester, polyurethane, polytetrafluoroethylene and the like. The adhesive selection may be based the particular tubing material and assembly modes. As is shown in FIG. 7, formation of an adhesive bonding layer 50 between flexible tube 12 and needle portion 24 may be facilitated by at least one opening 52 located distally in tube portion 12 for introduction of the adhesive 50 into an overlap area 54 between the needle portion and the tube bore. Introduction of adhesive 50 through the sidewall substantially reduces incidence of needle portion passageway 28 being blocked by excess adhesive during assembly.

Figure 8:
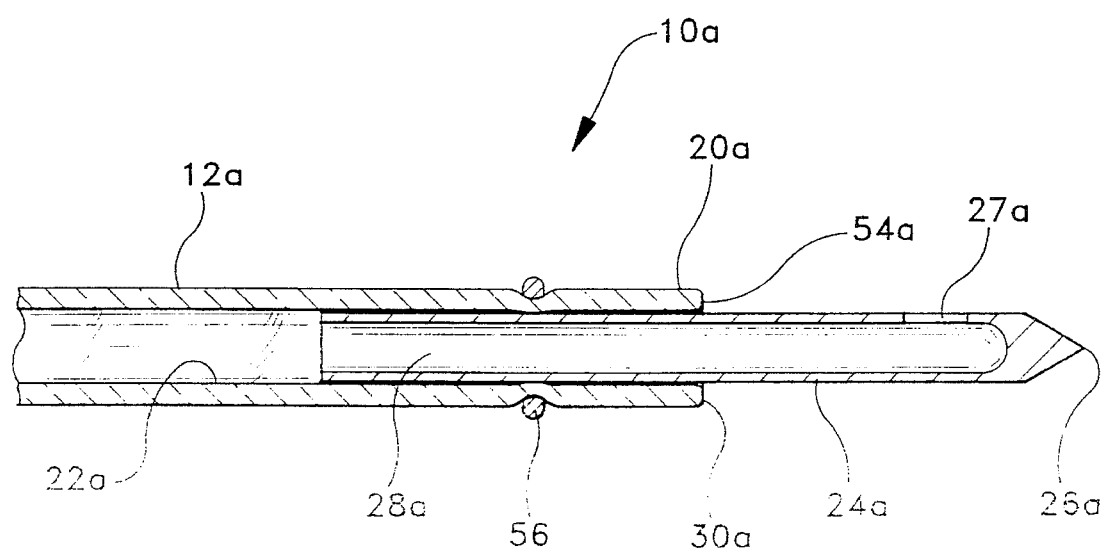
FIG. 8 is an enlarged cross-section of an alternate embodiment of the distal portion of the assembly of the present invention.

Referring now to FIG. 8, an alternative embodiment of the assembly is illustrated. In this alternative embodiment, the structure of the assembly is substantially similar to the embodiment shown in FIGS. 1–7. Accordingly, substantially similar components that perform substantially similar functions will be numbered identically to those components of the embodiment of FIGS. 1–7 except that a suffix "a" will be used to identify those components in FIG. 8.

Alternatively, needle portion 24a may be attached within bore 22a by means of at least one external band 56 crimped about tube 12a in the overlap area 54a with needle portion 24a. The crimped band serves to secure and seal portion 24a within tube bore 22a.

The kit may further include a guide wire stylet (not shown) to occlude needle port opening 48 and stiffen the assembly during the dural membrane penetration. The guide wire would then be removed to confirm placement by aspiration of cerebrospinal fluid. The kit may further include a filter for the medicament and an adapter to allow connection of a delivery device such as a syringe or infusion apparatus to the proximal end of the catheter. A Tuohy-Borst type adapter would be preferred. Additionally, the kit may include disinfectant skin preparation pads, adhesive tape, gloves and the like, if desired. The kit may be sealed in a package which provides a shelf package resistant to microorganisms, exposed to conditions such as ionizing radiation, sterilant gas and the like; the exposure would render any microorganisms contained within the package non-viable. Rendering any microorganisms present nonviable would thus provide a sterile ready-to-use procedure kit. One skilled in the art will recognize the necessity of ensuring that the materials used in the kit and the adhesive would be tolerant of the sterilization conditions and compatible with each other.

Thus it can be seen that the presently invented assembly, method and kit provide an improvement to the art of delivery of medicaments to the subarachnoid space and address the problems present in the earlier used devices and techniques.

What is claimed is:

1. A kit useful for introducing an injectable medicament into the subarachnoid space of a patient comprising:

a device for gaining access to the subarachnoid space consisting essentially of an epidural needle having a distal tip and a bore therethrough and a catheter/needle assembly comprising an elongate flexible tube portion sized to fit within said bore of said epidural needle, said tube having a proximal end, a distal end and a hollow bore therethrough, and an elongate needle portion having a distal point and a passageway therethrough being fit within, fixedly attached to and fluidly sealing said hollow bore of said flexible tube, said point projecting distally a distance beyond said distal end of said flexible tube, said passageway of said needle portion fluidly communicative with said hollow bore of said tube, and said distal end of said tube forming a shoulder projecting radially outwardly at said needle portion for providing a resistance to penetration of said tube into the subarachnoid space.

2. The kit of claim 1 further comprises a stylet for occluding said distal tip of said epidural needle.

3. The kit of claim 1 wherein said assembly further comprising a removable guidewire stylet.

4. The kit of claim 1 further including means for fluidly tightly attaching a delivery device for injectable medicaments to said proximal end of said assembly.

5. The kit of claim 1 wherein said means for fluidly tightly attaching a delivery device to said proximal end of said assembly is a Tuohy-Borst type adapter.

6. The kit of claim 1 further including filter means for the injectable medicament.

7. The kit of claim 1 wherein said epidural needle is sized from 15 to 3 gauge, said distance said elongate distal needle portion projects beyond said tube is within the range of 9 mm to 13 mm, said distal point of said needle portion is a closed tip having at least one side opening, and said assembly has an overall length of about 50 cm to 100 cm.

8. The kit of claim 1 further arranged in a unit package, sealed and exposed to conditions that render any microorganisms present therein nonviable.

9. The kit of claim 1 wherein said epidural needle has a straight bevel point at said distal tip formed at an angle from 30 to 50 degrees to a longitudinal axis of said needle.

10. The kit of claim 1 wherein said epidural needle is a Crawford-type needle having a straight bevel point at said distal tip formed at an angle about 40 degrees to a longitudinal axis of said needle.

11. The kit of claim 1 wherein the overall length of said assembly from said flexible tube portion proximal end to said needle portion distal point is about 50 cm to 100 cm.

12. The kit of claim 1 wherein the overall length of said assembly from said flexible tube portion proximal end to said needle portion distal point is about 76 cm.

13. A method for introducing an injectable medicament into the subarachnoid space of a patient comprising:

introducing an epidural needle having a distal point and a bore therethrough into an epidural space of a patient until said distal point of said epidural needle is in close approximation to the dural membrane;

advancing a catheter/needle assembly through said bore of said epidural needle, said assembly comprising an elongate flexible tube portion sized to fit within said bore of said epidural needle, said tube portion having a distal end and a hollow bore therethrough, said tube portion having a length greater than said epidural needle said assembly further comprising an elongate needle portion having a distal point and a passageway therethrough, said needle portion being fit within, fixedly attached and fluidly sealed in said hollow bore of said flexible tube, said point of said needle portion distally projecting a distance from said distal end of said flexible tube, said passageway fluidly communicative with said bore of said tube, said distal end of said flexible tube forming a shoulder projecting radially outwardly from said needle portion, until said elongate needle portion extends beyond said distal point of said epidural needle;

penetrating the dural membrane with said needle portion so that said bore of said assembly is in fluid communication with said subarachnoid space and said shoulder contacts the dural membrane providing a resistance to penetration of said flexible tube into the subarachnoid space;

withdrawing said epidural needle from said patient thereby leaving said catheter/needle assembly in the subarachnoid space; and introducing the medicament into the subarachnoid space of the patient through said hollow bore of said assembly.

14. The method of claim 13 further including aspirating cerebrospinal fluid through said assembly prior to said withdrawing said epidural needle step to confirm that the dural membrane has been penetrated.

15. The method of claim 13 wherein said distal point of said needle portion is closed and said needle portion has at least one side port.

16. The method of claim 13 wherein said distance said needle point projects beyond said tube is within the range of about 9 mm to 13 mm.

17. The method of claim 13 wherein said distance said needle point projects beyond said tube is about 11 mm.

18. The method of claim 13 wherein said epidural needle is sized from 16 to 25 gauge.

19. The method of claim 13 wherein said assembly has an overall length from said flexible tube portion proximal end to said needle portion distal point of about 50 cm to 100 cm.

20. The method of claim 13 wherein said assembly has an overall length from said flexible tube portion proximal end to said needle portion distal point of about 76 cm.

21. The method of claim 13 wherein said needle portion is 25 to 30 gauge and about 15 mm to 25 mm long.

* * * * *